US012773499B2

(12) United States Patent
Haslam et al.

(10) Patent No.: US 12,773,499 B2
(45) Date of Patent: Oct. 27, 2026

(54) LIVING HINGE SEAL FOR SILICONE-FREE SYRINGE BARREL

(71) Applicant: Merit Medical Systems, Inc., South Jordan, UT (US)

(72) Inventors: Michael Dean Haslam, Sandy, UT (US); Richard P. Jenkins, Bluffdale, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 964 days.

(21) Appl. No.: 18/051,621

(22) Filed: Nov. 1, 2022

(65) Prior Publication Data

US 2023/0133890 A1 May 4, 2023

Related U.S. Application Data

(60) Provisional application No. 63/275,183, filed on Nov. 3, 2021.

(51) Int. Cl.
*A61M 5/315* (2006.01)
*A61M 5/31* (2006.01)

(52) U.S. Cl.
CPC ...... *A61M 5/31513* (2013.01); *A61M 5/3129* (2013.01); *A61M 2207/10* (2013.01)

(58) Field of Classification Search
CPC ................................................ A61M 5/31513
See application file for complete search history.

(56) References Cited

U.S. PATENT DOCUMENTS

| | | | |
|---|---|---|---|
| 3,135,260 | A | 6/1964 | Hamilton |
| 4,543,093 | A | 9/1985 | Christinger |
| 5,181,912 | A | 1/1993 | Hammett |
| 7,087,037 | B2 | 8/2006 | Chiba et al. |
| 10,653,845 | B2 | 5/2020 | Butts et al. |
| 10,737,033 | B2 | 8/2020 | Butts et al. |

(Continued)

FOREIGN PATENT DOCUMENTS

JP 2002159574 A 6/2002

OTHER PUBLICATIONS

International Search Report and Written Opinion dated Mar. 8, 2023 for PCT/US2022/079058.

(Continued)

*Primary Examiner* — Bradley J Osinski
(74) *Attorney, Agent, or Firm* — Dorsey & Whitney LLP

(57) ABSTRACT

A syringe assembly void of silicone is disclosed. The syringe assembly includes a syringe plunger and a syringe barrel. The syringe plunger includes a handle and a plunger tip. The plunger tip includes a wiper extending from a hinge configured to allow the wiper to flex proximally and distally. The wiper includes a proximal circumferential seal and a distal circumferential seal. The proximal circumferential seal is configured to seal against an internal surface of the syringe barrel when the syringe plunger is displaced proximally and a negative pressure is generated within the syringe barrel. The distal circumferential seal is configured to seal against the internal surface of the syringe barrel when the syringe plunger is displaced distally and a positive pressure is generated within the syringe barrel. The syringe barrel includes internal detents to retain the syringe plunger within the syringe barrel.

16 Claims, 9 Drawing Sheets

(56) References Cited

U.S. PATENT DOCUMENTS

| | | | | |
|---|---|---|---|---|
| 2004/0010238 | A1* | 1/2004 | Manera | A61J 7/0053 604/289 |
| 2008/0083789 | A1 | 4/2008 | Brugner | |
| 2009/0099525 | A1* | 4/2009 | Lawson | A61M 5/14244 604/154 |
| 2011/0204097 | A1 | 8/2011 | Buehler et al. | |
| 2012/0253291 | A1 | 10/2012 | Ivosevic | |
| 2017/0066171 | A1 | 3/2017 | Giraud et al. | |
| 2019/0009034 | A1* | 1/2019 | Dietl | A61M 5/31513 |
| 2020/0129703 | A1 | 4/2020 | Prasad et al. | |
| 2021/0121670 | A1 | 4/2021 | Lee | |

OTHER PUBLICATIONS

European Search Report dated Aug. 1, 2025 for EP22890981.8.

Extended European Search Report dated Oct. 22, 2025 for EP22890981.8.

* cited by examiner

LIVING HINGE SEAL FOR SILICONE-FREE SYRINGE BARREL

RELATED APPLICATIONS

This application claims priority to U.S. Provisional Application No. 63/275,183, filed on Nov. 3, 2021 and titled, "Living Hinge Seal for Silicone-Free Syringe Barrel," which is hereby incorporated by reference in its entirety.

TECHNICAL FIELD

The present disclosure relates generally to medical devices. In some instances, the present disclosure relates to a lubrication-free syringe used to deliver fluid to or withdraw fluid from a patient. In some embodiments, the present disclosure relates to a syringe plunger having a tip seal configured to permit axial translation of a plunger within a lubrication-free syringe barrel.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
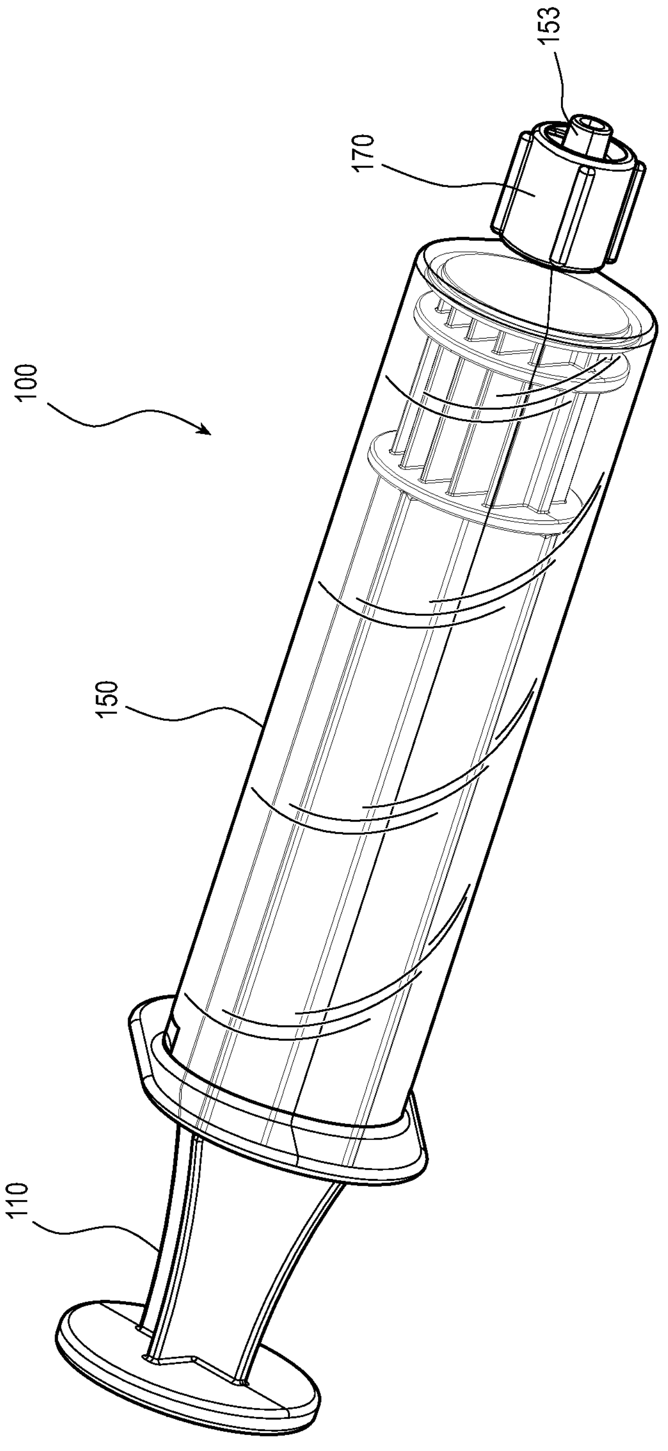
FIG. 1 is a perspective view of an embodiment of a syringe.

A syringe may be used to deliver fluids to or withdraw fluids from a patient. In certain instances, some components of the syringe (e.g., barrel, plunger tip) are coated with a lubricant, such as silicone oil, to facilitate or ease axial translation of a plunger within the barrel. However, silicone oil or other lubricants can negatively react with certain medicaments disposed within the barrel. For example, particles comprising poly vinyl alcohol agglomerate when interacting with silicone oil, sodium tetradecyl sulfate foam is defoamed when interacting with silicone oil, and silicone oil has a negative effect when injected into the eye.

Embodiments herein describe embodiments of syringes free of a lubricant, such as silicone oil. In some embodiments within the scope of this disclosure, the syringe includes a barrel defining a reservoir, a syringe plunger, and a Luer lock fitting. The syringe plunger includes an integrally formed handle and a plunger tip disposed at a distal end of the handle. The plunger tip includes a wiper portion having two seals, a pressure seal and a vacuum seal, configured to sealingly engage with an internal surface of the barrel. A flexing hinge couples the wiper portion to a central portion of the plunger tip. The flexing hinge allows the wiper portion to be proximally deflected as the syringe plunger is inserted into the reservoir. The flexing hinge also allows the wiper portion to rock from a pressure state where the pressure seal seals against the internal surface of the barrel when the reservoir is pressurized by distal movement of the syringe plunger and a vacuum state where the vacuum seal seals against the internal surface of the barrel when a vacuum or negative pressure is formed in the reservoir by proximal movement of the syringe plunger.

The syringe plunger may be formed from a material having a low co-efficient of friction to allow the seals to slide against the internal surface of the barrel without adding a lubricant to the seals and/or the internal surface. For example, the syringe plunger may be formed from high density polyethylene (HDPE), polypropylene, nylon, low density polyethylene (LDPE), or polyoxy methylene (POM). Other materials are contemplated. In some embodiments, a syringe plunger formed from HDPE is gamma irradiated to reduce the co-efficient of friction relative to a non-irradiated syringe plunger. The syringe plunger may be formed using an injection molding process. In some such embodiments, a cavity of a mold used to form the syringe plunger has parting lines along a length of the handle and circumferentially at a proximal end of the plunger tip such that a parting line does not cross the seals to prevent mold flashing from forming across the seals. If the mold flashing were to cross the seals, the mold flashing may cause fluid leakage at the plunger tip adjacent the mold flashing.

The barrel may include detents formed at a proximal end following insertion of the syringe plunger. The barrel may also include a zero draft internal diameter where the internal diameter is equivalent at a proximal end and a distal end of the barrel. Furthermore, in some embodiments, the barrel is formed of a clear, rigid thermoplastic material, such as polycarbonate (PC), polypropylene, polystyrene, polypropylene, cyclo-olefin polymer (COP), cyclo-olefin copolymer (COC), amorphous nylon or glass.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Figure 2:
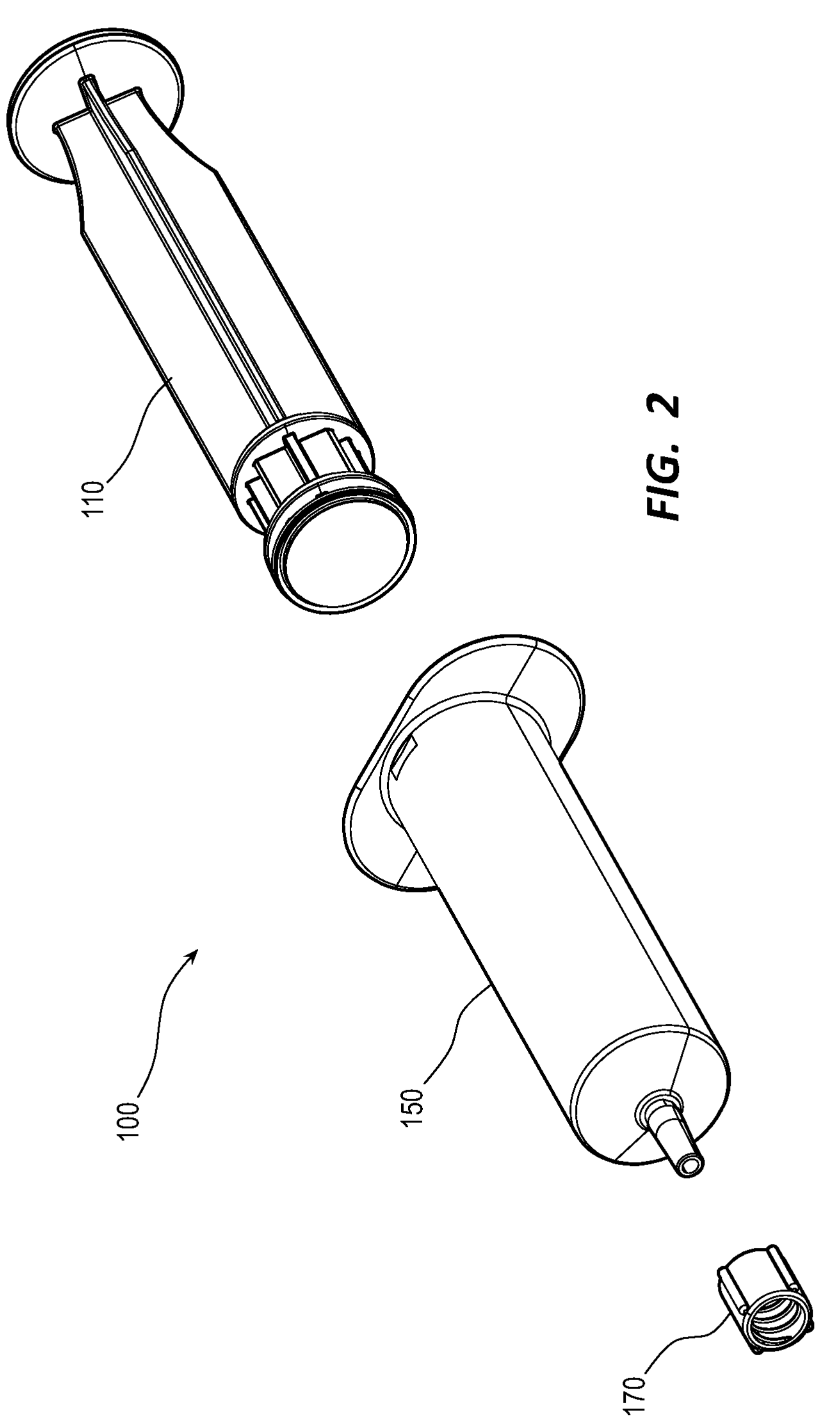
FIG. 2 is a perspective exploded view of the syringe of FIG. 1.
Figure 3A:
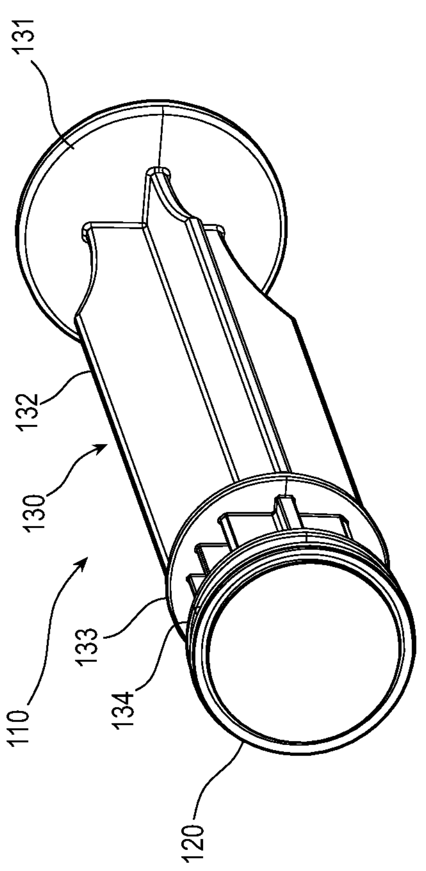
FIG. 3A is a perspective view of an embodiment of a syringe plunger of the syringe of FIG. 1.
Figure 3B:
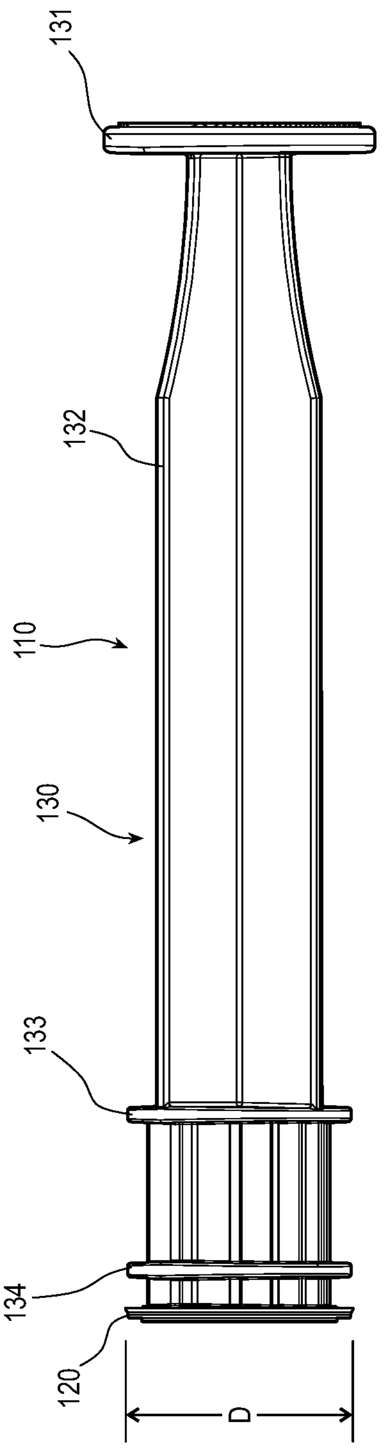
FIG. 3B is a side view of the plunger of the syringe of FIG. 1.
Figure 6A:
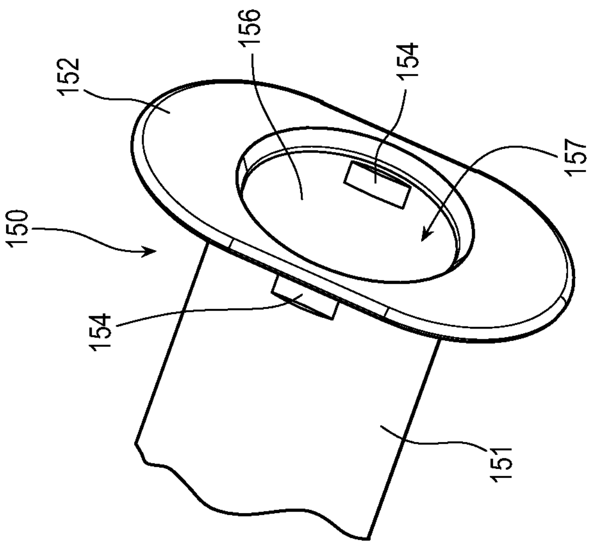
FIG. 6A is a perspective view of a proximal portion of the syringe barrel of FIG. 6.
Figure 6:
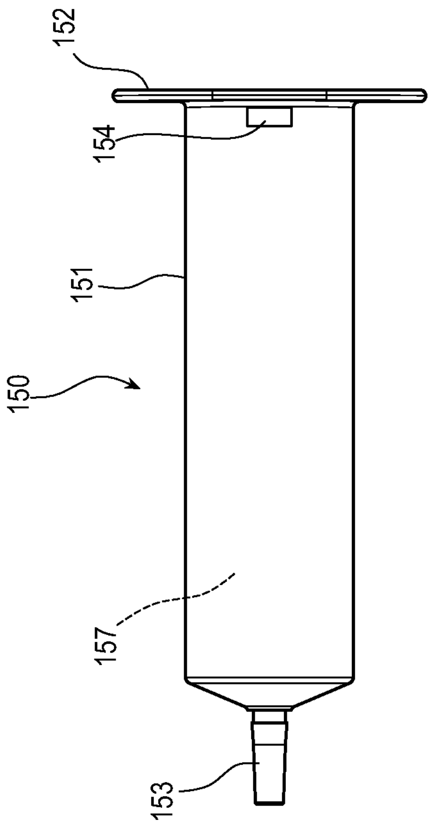
FIG. 6 is a side view of an embodiment of a syringe barrel of the syringe of FIG. 1.
Figure 7:
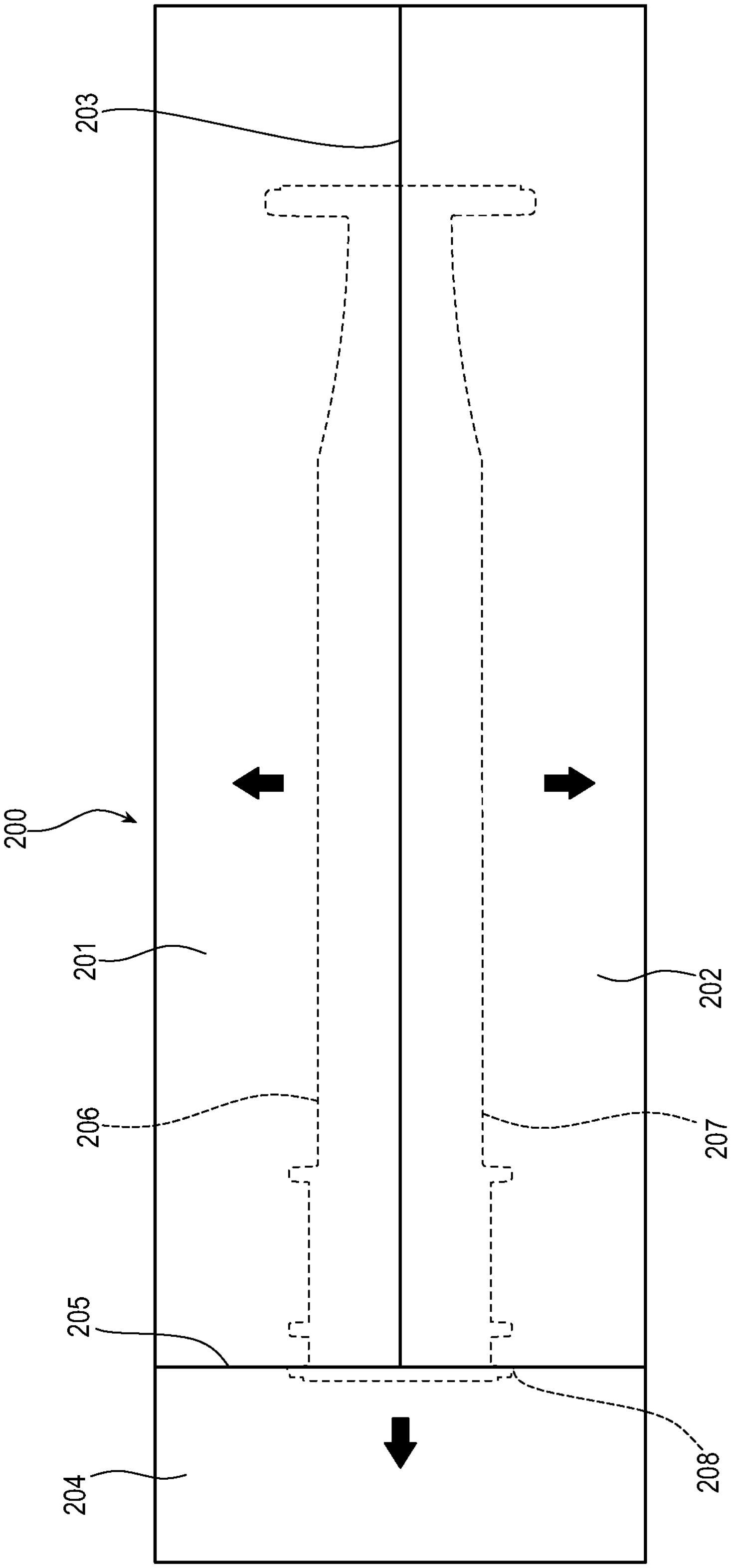
FIG. 7 is side view of an embodiment of a syringe plunger injection mold.

FIGS. 1 and 2 illustrate an embodiment of a syringe. FIGS. 3A and 3B illustrate an embodiment of a syringe plunger of the syringe. FIGS. 4A-5B illustrate an embodiment of a plunger seal of the syringe plunger. FIGS. 6 and 6A illustrate an embodiment of a syringe barrel of the syringe. FIG. 7 illustrates an embodiment of a syringe plunger injection mold. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

As illustrated in FIGS. 1 and 2, a syringe 100 may be understood to include two broad groups of components; each group may have numerous subcomponents and parts. The two broad component groups are: a syringe plunger 110 and a syringe barrel 150. In the illustrated embodiment, a Luer-lock nut 170 is coupled to a distal end of the syringe barrel 150 to form a male Luer-lock fitting. In some embodiments, the syringe barrel 150 and the Luer-lock nut 170 comprise a unibody construct. In other embodiments, a male Luer-slip fitting is disposed at the distal end of the syringe barrel 150. Other coupling features or tips are likewise within the scope of this disclosure.

As illustrated in FIGS. 3A and 3B, the syringe plunger 110 may comprise a plunger tip 120 and a handle 130. The handle 130 may be a unibody construct formed by an injection molding manufacturing technique as described below. The material of the handle 130 can include any suitable material having a low coefficient of friction on glass or PC to facilitate sliding movement of the syringe plunger 110 within the syringe barrel 150 without use of a lubricant. For example, the static and/or kinetic coefficient of friction of the material of the handle 130 can be relatively low. In some embodiments, the static and kinetic coefficient of frictions may be substantially equivalent to prevent a stick-slip behavior where the plunger sticks to the syringe barrel 150 and then suddenly slips. Examples of suitable materials include HDPE, polypropylene, nylon, LDPE, or POM. Other materials are contemplated.

The handle 130 of the depicted embodiment includes a thumb pad 131 disposed at a proximal end of the handle 130. The thumb pad 131 may be used to manipulate the syringe plunger 110 relative to the syringe barrel 150 to inject a fluid, such as a medicament, from the syringe barrel 150 or to draw the fluid into the syringe barrel 150. A proximal surface of the thumb pad 131 can include features to enhance a user's interaction with the thumb pad 131. The features may include ribs, grooves, bumps, divots, surface texturing, etc. In other embodiments, the thumb pad 131 may be a ring configured to receive a user's digit, such as a thumb.

In some embodiments, a plurality of ribs 132 are disposed between the thumb pad 131 and the plunger tip 120. The number of ribs 132 may be three, four, five, six, or more. In another embodiment, the handle 130 may include an elongate cylinder disposed between the thumb pad 130 and the plunger tip 120. A width of the handle 130 transversely across the ribs 132 may be smaller than a diameter of a bore 157 of the syringe barrel 150 such that the ribs 132 help to maintain co-axial alignment of the plunger tip 120 with the bore 157 of the syringe barrel 150. For example, the width of the handle may be from about 0.10 millimeter to about 0.25 millimeter smaller than the diameter of the bore 157. This configuration may be configured to help to ensure substantial equal circumferential sealing of the plunger tip seals 123, 124 with an internal surface 156 of the syringe barrel 150.

A proximal alignment disk 133 and a distal alignment disk 134 can be disposed at a distal portion of the handle 130 adjacent or near the plunger tip 120. The disks 133, 134 may be longitudinally spaced apart and have a diameter substantially equivalent to the diameter of the handle 130, such that the disks 133, 134 help to maintain co-axial alignment of the plunger tip 120 with the bore 157 of the syringe barrel 150. This configuration helps to ensure substantial equal circumferential sealing of the plunger tip seals 123, 124 with an internal surface 156 of the syringe barrel 150.

In the illustrated embodiment, as shown in FIGS. 3A and 3B, the plunger tip 120 is coupled to and disposed at a distal end of the handle 130. The plunger tip 120 is configured to slidingly seal against the internal surface 156 of the barrel 150 without the use of a lubricant. In the embodiment illustrated in FIG. 4A, the plunger tip 120 includes a wiper 121, a hinge 122, and a central portion 126. The central portion 126 is in axial alignment with the handle 130. The hinge 122 is circumferentially coupled to the central portion 126. The hinge 122 includes a circumferential necked down portion 127 such that the hinge 122 is configured to flex proximally and distally relative to a longitudinal axis of the syringe plunger 110. The necked down portion 127 may have a thickness ranging from about 0.2 millimeter to about 0.8 millimeter.

Figure 4A:
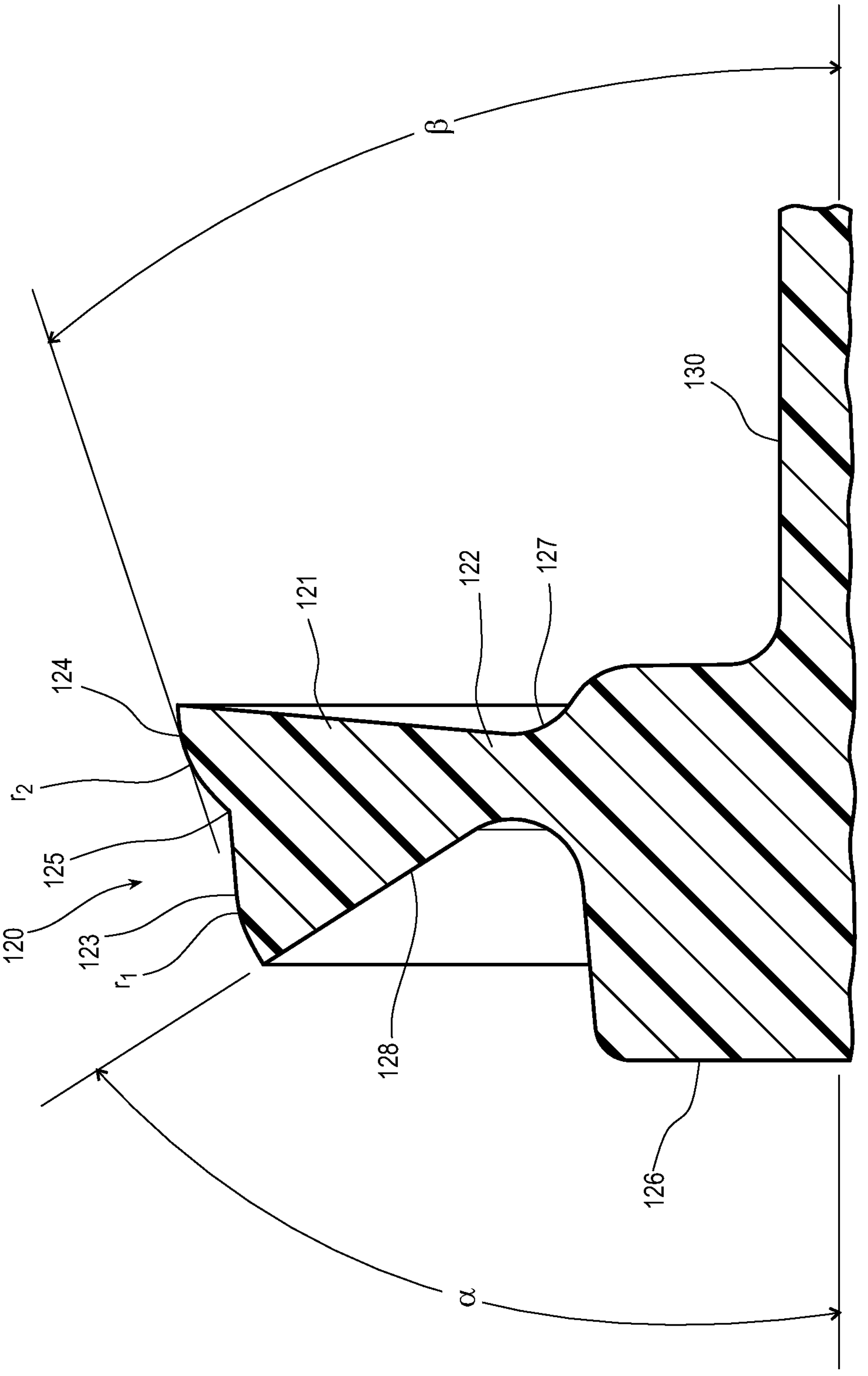
FIG. 4A is a cross-sectional view of a plunger seal of the syringe plunger of FIGS. 3A and 3B in a formed state.
Figure 4B:
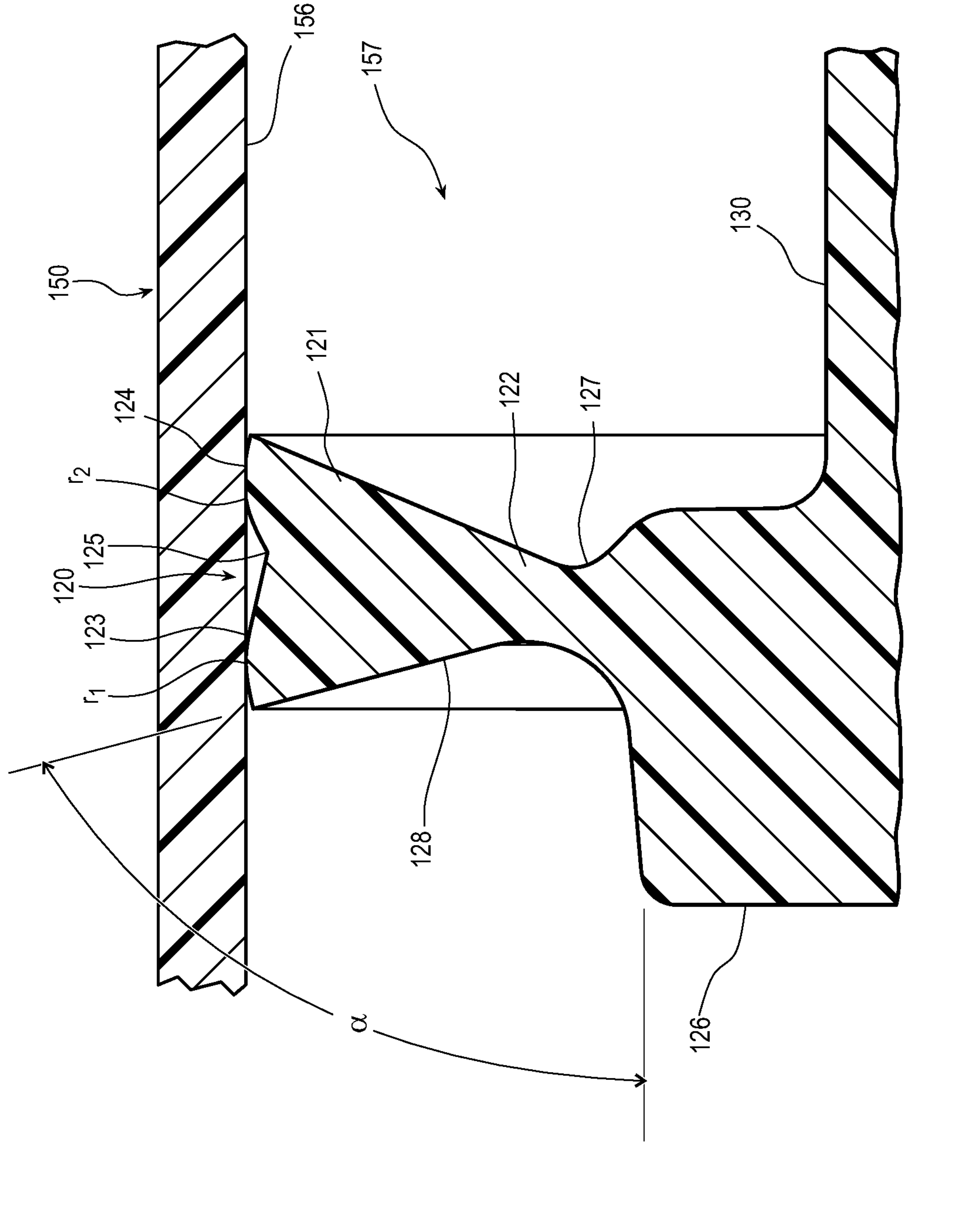
FIG. 4B is a cross-sectional view of the plunger seal of the syringe plunger of FIGS. 3A and 3B in a deflected state.

The wiper 121 extends radially outward from the hinge 122. The wiper 121 includes a circumferential distal seal 123, a circumferential proximal seal 124, and a circumferential recess 125 disposed between the distal seal 123 and the proximal seal 124. A distal surface 128 of the wiper 121 includes an angle $\alpha$ ranging from about 30 degrees to about 80 degrees relative to the longitudinal axis of the syringe plunger 110 as shown in FIG. 4A, prior to insertion of the syringe plunger 110 into the bore 157 of the syringe barrel 150. The wiper 121 may be proximally deflected, as shown in FIG. 4B, when the syringe plunger 110 is inserted into the bore 157 as the wiper 121 engages with the internal surface 156 of the bore 157 to ensure sealing engagement of the seals 123, 124 with the internal surface 156. The angle $\alpha$ may range from about 5 degrees to about 30 degrees following insertion of the plunger tip 120 into the bore 157. An outside diameter D of the wiper 121 (measurement D shown in FIG. 3B) can be larger than the diameter of the bore 157.

As depicted in the embodiment of FIG. 4A, the distal seal 123 includes a convex radius $r_1$. The proximal seal 124 includes a convex radius $r_2$. The seals 123, 124 are disposed at an angle $\beta$ relative to the longitudinal axis of the syringe plunger 110 prior to insertion of the plunger tip 120 into the bore 157, as shown in FIG. 4A. The seals 123, 124 are disposed substantially parallel to the longitudinal axis of the syringe plunger 110 following deflection of the hinge 122 when the plunger tip 120 is inserted into the bore 157, as shown in FIG. 4B. The recess 125 is disposed between the seals 123, 124 and has a depth relative to a tangent line between the seals 123, 124 ranging from about 0.05 millimeter to about 0.4 millimeter.

Figure 5A:
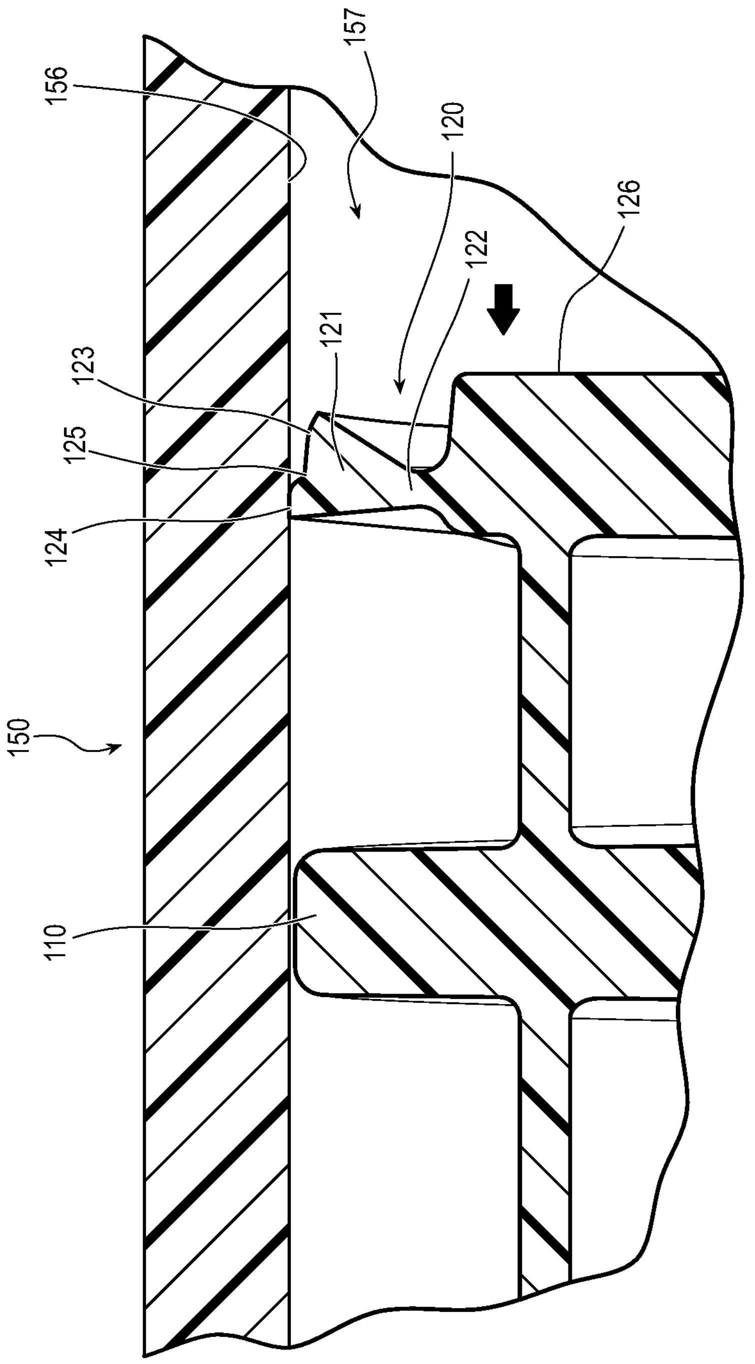
FIG. 5A is a perspective view of a portion of the syringe of FIG. 1 with the plunger seal in a pressure state.
Figure 5B:
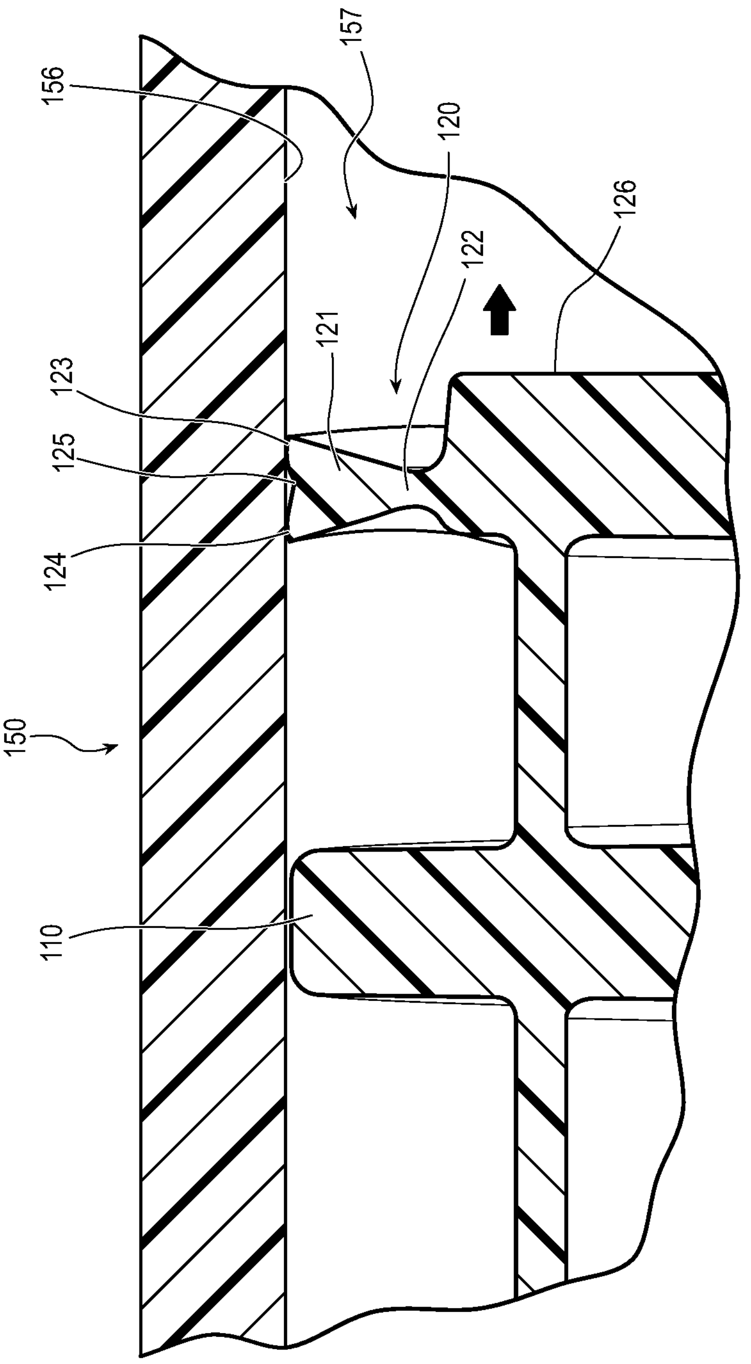
FIG. 5B is a perspective view of a portion of the syringe of FIG. 1 with the plunger seal in a vacuum state.

FIGS. 5A and 5B illustrate the plunger tip 120 in a vacuum state and a pressure state, respectively. As shown in FIG. 5A, when the plunger tip 120 is displaced proximally, direction of arrow, within the bore 157 of the syringe barrel 150, a vacuum or negative pressure can be generated within the bore 157 distal of the plunger tip 120. When the vacuum is generated, the wiper 121 may be displaced or flexed distally about the hinge 122 such that the proximal seal 124 is biased toward the internal surface 156 to ensure sealing engagement of the proximal seal 124 with the internal surface 156. As shown in FIG. 5B, when the plunger tip 120 is displaced distally, direction of arrow, within the bore 157 of the syringe barrel 150, a positive pressure can be generated within the bore 157 distal of the plunger tip 120. When the positive pressure is generated, the wiper 121 may be displaced or flexed proximally about the hinge 122 such that the distal seal 123 is biased toward the internal surface 156 to ensure sealing engagement of the distal seal 123 with the internal surface 156.

FIGS. 6 and 6A illustrate an embodiment of the syringe barrel 150. The syringe barrel 150 can be formed as a unibody construct using any suitable technique, such as injection molding, 3D printing, machining, over-molding, etc. The syringe barrel 150 may be formed of any suitable transparent or translucent rigid or semi-rigid material. For example, the material of the syringe barrel 150 can be glass, PC, polypropylene, cyclo-olefin polymer (COP), cyclo-olefin copolymer (COC), or amorphous nylon. Other materials are contemplated. As illustrated, the syringe barrel 150 includes an elongate, tubular body 151 having an internal surface 156 that defines the bore 157 extending therethrough. The bore 157 is configured as a reservoir to contain fluid, such as a medicament to be injected into a patient. A male Luer fitting 153 is disposed at a distal end of the body 151 and is in fluid communication with the bore 157. The male Luer-lock nut 170 may be coupled to the male Luer fitting 153 as shown in FIG. 1. A flange 152 is disposed at a proximal end of the body 151. The flange 152 extends radially outward from the body 151 and can be used to grip the syringe barrel 150 during use.

As depicted, the body 151 includes an internal detent 154 disposed adjacent the proximal end to retain the syringe plunger 110 within the bore 157. The number of detents 154 may be one, two, three, four, or more that are spaced equidistantly around a circumference of the body 151. A height of the detent 154 may range from about 2.0 millimeters to about 2.5 millimeters from the internal surface 156. In other words, the proximal disk 133 has a diameter larger than a transverse distance between the detents 154 such that the proximal disk 133 can engage the detents 154 when the syringe plunger 110 is displaced proximally to prevent the syringe plunger 110 from inadvertently being removed from the syringe barrel 150. The detent 154 can include a rectangular, circular, or dome shape. Other shapes are contemplated. The detent 154 may be formed in the body 151 following insertion of the plunger tip 120 into the bore 157 using pressure and/or heat applied by a detent forming tool.

FIG. 7 illustrates an embodiment of an injection mold 200 that may be used to form the syringe plunger 110. As illustrated, the injection mold 200 may include an upper mold portion 201, a lower mold portion 202, a slide portion 204, and a cavity 206. The cavity 206 includes a handle portion 207 disposed within the upper mold portion 201 and the lower mold portion 202. The handle portion 207 includes a negative shape of the handle 130 of the syringe plunger 110 to receive molten material to form the handle 130 as previously described. A longitudinal parting line 203 divides the upper mold portion 210 from the lower mold portion 202 and extends along a longitudinal axis of the handle portion 207.

A plunger tip portion 208 of the cavity 205 may be disposed within the slide portion 204. The plunger tip portion 208 includes a negative shape of the plunger tip 120 of the syringe plunger 110. A vertical parting line 205 divides the slide portion 204 from the upper and lower mold portions 201, 202. Thus, the plunger tip portion 208 may be configured such that the vertical parting line 205 does not cross into the plunger tip portion 208 of the cavity 206.

In use, molten material is injected into the cavity 206 to form the syringe plunger 110. Following cooling of the molten material, the upper mold portion 201 is separated from the lower mold portion 202 along the parting line 203 releasing the handle 130 of the syringe plunger 110 from the handle portion 207 of the cavity 206, as indicated by the arrows. The upper and lower mold portions 201, 202 are also moved along the vertical parting line 205 to expose a proximal surface of the plunger tip 120 of the syringe plunger 110. The slide portion 204 is moved away from the upper mold portion 201 and the lower mold portion 202, as indicated by the arrow. The plunger tip 120 is ejected from the plunger tip portion 208. The formed plunger tip 120 is free of mold flashing across the seals 123, 124 because the vertical parting line 205 did not cross the seals 123, 124. This design may be configured to prevent leakage around the plunger tip 120. Mold flashing crossing the seals 123, 124 may prevent the plunger tip 120 from sealing with the internal surface 156 of the syringe barrel 150. In other words, mold flashing on the seals 123, 124 may allow fluid to leak around the plunger tip 120. Thus, embodiments wherein the seals 123, 124 are free of mold flashing may be configured to facilitate sealing.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of manufacturing a syringe plunger may include one or more of the following steps: injecting a molten material into a cavity of the mold; wherein the cavity comprises a syringe plunger shaped void comprising: a plunger tip portion comprising a first seal portion and a second seal portion, and a plunger handle portion, a longitudinal parting line extending proximally of a plunger tip portion of the cavity, and a circumferential parting line disposed proximally of the plunger tip portion; parting the mold along the longitudinal parting line; and ejecting a plunger tip of a molded syringe plunger from the plunger tip portion of the cavity, wherein the plunger tip is free of molding flashing extending longitudinally across a first seal and a second seal of the plunger tip. Other steps are also contemplated.

In the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest to the practitioner during use.

"Fluid" is used in its broadest sense, to refer to any fluid, including both liquids and gases as well as solutions, compounds, suspensions, body fluids, etc., which generally behave as fluids.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially equivalent" is recited with respect to a feature, it is understood that in further embodiments, the feature can have a precisely equivalent configuration.

The terms "a" and "an" can be described as one, but not limited to one. For example, although the disclosure may recite a housing having "a stopper," the disclosure also contemplates that the housing can have two or more stoppers.

Unless otherwise stated, all ranges include both endpoints and all numbers between the endpoints.

Recitation in the claims of the term "first" with respect to a feature or element does not necessarily imply the existence of a second or additional such feature or element.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A syringe, comprising:

a barrel defining a bore comprising an internal surface, wherein the internal surface is free of a lubricating material; and a syringe plunger slidingly disposable within the bore, the syringe plunger comprising:

a handle portion; and a plunger tip disposed at a distal end of the handle portion, the plunger tip comprising:

a central portion in axial alignment with the handle portion;

a circumferential hinge circumferentially coupled to the central portion; and a wiper portion circumferentially coupled to the circumferential hinge, the wiper portion comprising:

a first circumferential seal; and a second circumferential seal disposed distally of the first circumferential seal, wherein the first and second circumferential seals are free of a lubricating material, wherein the first and second circumferential seals slidingly engage with the internal surface of the bore, and wherein the circumferential hinge is biased distally when the plunger is displaced proximally within the bore to generate a vacuum in the bore, and wherein the first circumferential seal is biased toward the internal surface.

2. The syringe of claim 1, wherein a minimum thickness of the circumferential hinge is thinner than a thickness of the central portion and the wiper portion.

3. The syringe of claim 2, wherein the minimum thickness of the circumferential hinge ranges from 0.2 millimeter to 0.8 millimeter.

4. The syringe of claim 1, wherein the first circumferential seal comprises a convex shape.

5. The syringe of claim 1, wherein the second circumferential seal comprises a convex shape.

6. The syringe of claim 1, further comprising a circumferential recess disposed between the first circumferential seal and the second circumferential seal.

7. The syringe of claim 1, wherein the circumferential hinge is biased proximally when the plunger is displaced distally within the bore to generate a pressure in the bore, and wherein the second circumferential seal is biased toward the internal surface.

8. The syringe of claim 1, wherein the circumferential hinge is biased proximally when the plunger is inserted into the bore wherein the first and second circumferential seals contact the internal surface.

9. The syringe of claim 1, wherein the syringe plunger comprises a unibody construct.

10. The syringe of claim 1, wherein the syringe plunger comprises one or more of high density polyethylene, polypropylene, nylon, low density polyethylene, or polyoxy methylene.

11. The syringe of claim 1, wherein the handle portion comprises a disk configured to axially align the plunger tip with a longitudinal axis of the barrel.

12. The syringe of claim 1, wherein the handle portion comprises a plurality of longitudinal ribs configured to axially align the plunger tip with the longitudinal axis of the barrel.

13. The syringe of claim 1, wherein the barrel comprises a detent extending radially inward from the internal surface, and wherein the detent is configured to retain the plunger tip within the bore.

14. The syringe of claim 1, wherein the barrel comprises one or more of polycarbonate, polypropylene, polystyrene, polypropylene, cyclo-olefin polymer, cyclo-olefin copolymer, amorphous nylon or glass.

15. A syringe plunger, comprising:
- a handle portion; and
- a plunger tip disposed at a distal end of the handle portion, the plunger tip comprising:
  - a central portion in axial alignment with the handle portion;
  - a circumferential hinge circumferentially coupled to the central portion; and
  - a wiper portion circumferentially coupled to the circumferential hinge, the wiper portion comprising:
    - a proximal circumferential seal; and
    - a distal circumferential seal disposed distally of the first circumferential seal,
    - wherein the proximal and distal circumferential seals are free of mold flashing, and
    - wherein the circumferential hinge is biased distally when the plunger is displaced proximally within a syringe barrel to generate a vacuum in the syringe barrel, and wherein the proximal circumferential seal is biased toward an internal surface of the syringe barrel.

16. A syringe, comprising:
- a barrel defining a bore comprising an internal surface, wherein the internal surface is free of a lubricating material; and
- a syringe plunger slidingly disposable within the bore, the syringe plunger comprising:
  - a handle portion; and
  - a plunger tip disposed at a distal end of the handle portion, the plunger tip comprising:
    - a central portion in axial alignment with the handle portion;
    - a circumferential hinge circumferentially coupled to the central portion; and
    - a wiper portion circumferentially coupled to the circumferential hinge, the wiper portion comprising:
      - a first circumferential seal; and
      - a second circumferential seal disposed distally of the first circumferential seal,
      - wherein the first and second circumferential seals are free of a lubricating material,
      - wherein the first and second circumferential seals slidingly engage with the internal surface of the bore, and
      - wherein the circumferential hinge is biased proximally when the plunger is displaced distally within the bore to generate a pressure in the bore, and wherein the second circumferential seal is biased toward the internal surface.

* * * * *